(12) United States Patent
Takei et al.

(10) Patent No.: US 9,975,140 B2
(45) Date of Patent: May 22, 2018

(54) APPLICATOR THAT ALLOWS EASY MOUNTING AND REMOVAL OF CARTRIDGE

(71) Applicant: SHOFU INC., Kyoto-shi, Kyoto (JP)

(72) Inventors: Ryouji Takei, Soka (JP); Akira Yoneda, Soka (JP); Shuji Sakamoto, Kyoto (JP); Yusei Kadobayashi, Kyoto (JP)

(73) Assignee: SHOFU INC., Kyoto-Shi (JP)

( * ) Notice: Subject to any disclaimer, the term of this patent is extended or adjusted under 35 U.S.C. 154(b) by 4 days.

(21) Appl. No.: 15/206,458

(22) Filed: Jul. 11, 2016

(65) Prior Publication Data

US 2017/0014857 A1 Jan. 19, 2017

(30) Foreign Application Priority Data

Jul. 14, 2015 (JP) .................................. 2015-140833

(51) Int. Cl.
*B05C 17/005* (2006.01)
*A61M 5/24* (2006.01)
(Continued)

(52) U.S. Cl.
CPC .......... *B05C 17/00593* (2013.01); *A61C 5/62* (2017.02); *A61C 5/66* (2017.02);
(Continued)

(58) Field of Classification Search
CPC ........ B05C 17/00593; B05C 17/00596; B05C 17/00516; B05C 17/01; A61M 5/2425; A61C 5/62; A61C 5/66
(Continued)

(56) References Cited

U.S. PATENT DOCUMENTS 4,391,590 A * 7/1983 Dougherty ........... A61C 9/0026
433/90
5,061,179 A * 10/1991 Dragan .................... A61C 5/62
433/90
(Continued)

FOREIGN PATENT DOCUMENTS

| JP | 8-511961 | 12/1996 |
| JP | 2001-112782 | 4/2001 |
| WO | 95/00018 | 1/1995 |

OTHER PUBLICATIONS

European Search Report dated Nov. 18, 2016, 6 pages.

*Primary Examiner* — Nicholas J Weiss
(74) *Attorney, Agent, or Firm* — Rankin, Hill & Clark LLP

(57) ABSTRACT

A cartridge fitting portion of a cylindrical syringe made of a resin includes an end surface opening portion, a continuous opening portion continuous with the end surface opening portion, opened in a radial direction, and extending in an extending direction, and a recess portion configured to communicate with the end surface opening portion, the continuous opening portion, and an internal passage in a cylindrical body. The recess portion includes a flange fitting recess to be fitted with a flange portion of a cartridge, and a cylindrical portion fitting recess that communicates with the flange fitting recess and is fitted with a part of the cylindrical portion. A wall portion surrounding the cylindrical portion fitting recess of the cartridge fitting portion is configured to warp into snap engagement with the part of the cylindrical portion when the part of the cylindrical portion is inserted from the continuous opening portion.

2 Claims, 10 Drawing Sheets

(51) Int. Cl.
*A61C 5/62* (2017.01)
*A61C 5/66* (2017.01)
*B05C 17/01* (2006.01)

(52) U.S. Cl.
CPC ..... *A61M 5/2425* (2013.01); *B05C 17/00516* (2013.01); *B05C 17/00596* (2013.01); *B05C 17/01* (2013.01)

(58) Field of Classification Search
USPC .................................... 433/90; 604/232, 234
See application file for complete search history.

(56) References Cited

U.S. PATENT DOCUMENTS

| | | | | |
|---|---|---|---|---|
| 5,129,825 A | * | 7/1992 | Discko, Jr. ............... | A61C 5/62 222/325 |
| 5,267,859 A | * | 12/1993 | Discko, Jr. ........ | B05C 17/00593 433/89 |
| 5,306,147 A | * | 4/1994 | Dragan ................... | A61C 5/62 433/90 |
| D359,560 S | * | 6/1995 | Mitchell ...................... | D24/143 |
| 5,489,207 A | * | 2/1996 | Dragan ................... | A61C 5/62 433/90 |
| 5,692,642 A | * | 12/1997 | Brattesani ............... | B05C 17/01 221/199 |
| 5,743,431 A | * | 4/1998 | Brattesani ............... | B05C 17/01 222/1 |
| 6,312,254 B1 | * | 11/2001 | Friedman ................. | A61C 5/62 433/32 |
| 6,328,715 B1 | * | 12/2001 | Dragan ................... | A23G 9/24 604/232 |
| 6,652,494 B1 | * | 11/2003 | Dragan ................... | A23G 9/24 222/327 |
| 6,929,157 B2 | * | 8/2005 | Orecchia ........... | B05C 17/00593 222/326 |
| 7,954,672 B2 | * | 6/2011 | Keller ............... | B05C 17/00553 222/137 |
| 2002/0010430 A1 | | 1/2002 | Dragan et al. | |
| 2013/0216975 A1 | * | 8/2013 | Fritze ................... | A61C 19/063 433/90 |
| 2015/0342714 A1 | * | 12/2015 | Fritze ................... | A61C 19/063 433/90 |

* cited by examiner

*Fig.1A*
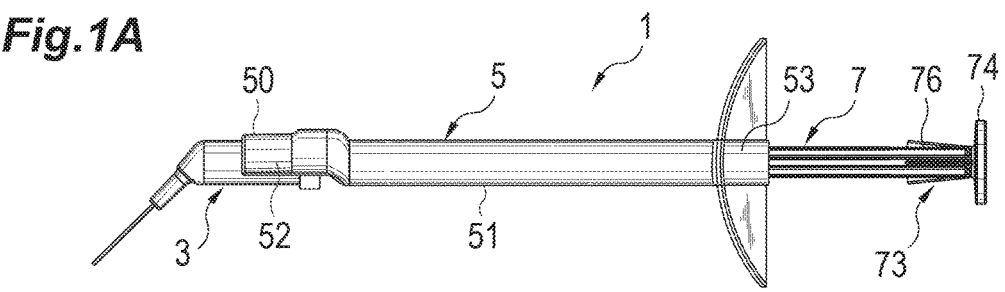
*Fig.1B*
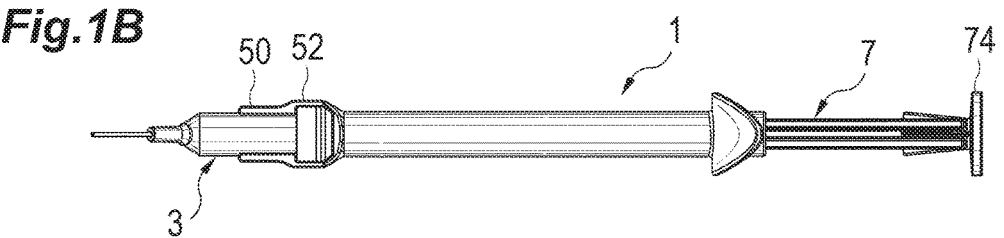
*Fig.1C*
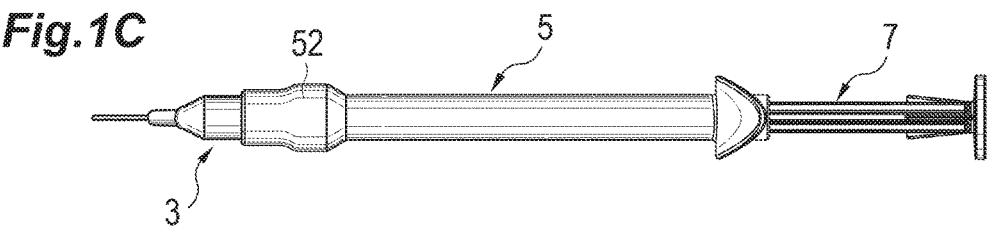
*Fig.1D* 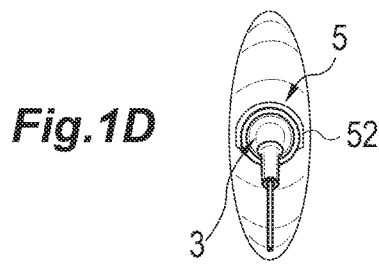 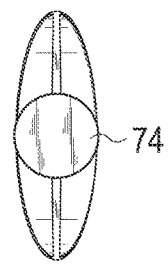 *Fig.1E*
*Fig.1F*
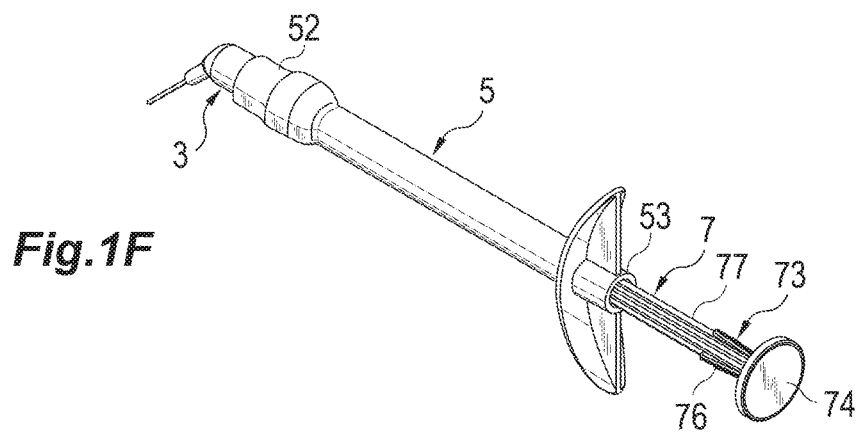

APPLICATOR THAT ALLOWS EASY MOUNTING AND REMOVAL OF CARTRIDGE

TECHNICAL FIELD

The present invention relates to an applicator that includes a cylindrical syringe including a cartridge fitting portion provided at one of two ends of the cylindrical syringe and configured to be fitted with a cartridge, and a plunger configured to be inserted into the cylindrical syringe and to press a piston inside the cartridge.

BACKGROUND ART

An example of an applicator, which includes a cylindrical syringe 526 and a plunger 26, is disclosed in FIG. 16 of JP 2001-112782 A. The cylindrical syringe 526 includes a cartridge fitting portion 527 configured to be fitted with a cartridge 210 which does not include a piston and the body of which is deformable to push out a content contained in the cartridge 210 from a nozzle portion 218. The plunger 26 is configured to be inserted into the cylindrical syringe 526, and includes an operated portion 42 extending through one of two ends of the cylindrical syringe 526 opposite to the cartridge fitting portion 527 and configured to be pressed by a finger of an operator. The cartridge fitting portion 527 is configured to be fitted with the cartridge 210 by moving the cartridge 210 close to the cartridge fitting portion 527. Judging from the sectional configuration of a cartridge fitting portion of an applicator of a so-called syringe gun type illustrated in FIG. 15, the cartridge fitting portion 527 is longer than the cartridge 210.

Another example of an applicator called a syringe gun is disclosed in FIGS. 1 and 2 of JP 08-511961 A. A cartridge fitting portion 22 of the syringe gun includes a flange 25 provided at a distal end portion of the cartridge fitting portion 22 and configured to be fitted with a groove 14 of a collar 13 provided at a rear end portion of a cartridge 11. When fitting the cartridge 11 with the cartridge fitting portion 22 and removing the cartridge 11 from the cartridge fitting portion 22, the groove 14 is inserted into the flange 25 and withdrawn from the flange 25. Inserting into and withdrawing from the flange 25 is simply equivalent to moving the cartridge 11 close to and away from the cartridge fitting portion 22, respectively. The cartridge fitting portion 22 is shaped such that an extra space is secured in rear of a plunger to allow for sliding of the cartridge between the groove 14 of the collar 13 of the cartridge 11 and the flange 25 of the cartridge fitting portion 22.

SUMMARY OF INVENTION

Technical Problem

Judging from the configurations of the applicator disclosed in 2001-112782 A, it is considered that the cylindrical syringe is made of metal and that the plunger is made of metal although not clearly stated in the document. The applicators made of metal advantageously have a high mechanical strength and can be repeatedly used, but are too expensive to be disposable. If the applicators are so expensive, expanded sales of the cartridges may be adversely affected.

The applicator disclosed in JP 08-511961 A includes main parts formed from plastic. However, the syringe gun is not disposable in consideration of its structure, is accordingly configured to allow ready mounting and removal of the cartridge, and is expensive.

An object of the present invention is to provide an applicator that is made of a resin, facilitates mounting and removal of a cartridge, and has a simple structure and is lower-priced than the conventional ones.

Solution to Problem

An applicator according to the present invention includes a cylindrical syringe made of a resin and a plunger made of a resin. The cylindrical syringe includes a cylindrical body having two ends. The cylindrical body includes a cartridge fitting portion at one of the two ends of the cylindrical body. The cartridge fitting portion is configured to be fitted with a cartridge which includes a cylindrical portion having two ends, having an opening portion and a flange portion at one of the two ends of the cylindrical portion, a nozzle portion provided at the other of the two ends of the cylindrical portion, and a piston disposed inside the cylindrical portion to push out a content contained in the cylindrical portion from the nozzle portion. The plunger has two ends, and includes a pressing portion provided at one of the two ends of the plunger and an operated portion provided at the other of the two ends of the plunger. The pressing portion is configured to be inserted into the syringe from the other of the two ends of the cylindrical body of the cylindrical syringe and to press the piston inside the cartridge fitted with the cartridge fitting portion. The operated portion extends through the other end of the cylindrical body of the cylindrical syringe and is configured to be pressed by a finger of an operator. The cartridge fitting portion includes an end surface opening portion opened in an extending direction in which the cylindrical body extends, a continuous opening portion continuous with the end surface opening portion, opened in a radial direction, and extending in the extending direction, and a recess portion configured to communicate with the end surface opening portion, the continuous opening portion, and an internal passage in the cylindrical body. The recess portion includes a flange fitting recess to be fitted with the flange portion of the cartridge, and a cylindrical portion fitting recess configured to communicate with the flange fitting recess and to be fitted with a part of the cylindrical portion. A wall portion surrounding the cylindrical portion fitting recess of the cartridge fitting portion is configured to warp into snap engagement with the part of the cylindrical portion when the part of the cylindrical portion is inserted from the continuous opening portion. Herein, the term "snap engagement" refers to engagement obtained when the wall portion surrounding the cylindrical portion fitting recess holds the cylindrical portion utilizing a force generated in the wall portion which has been deformed to be opened and then is going to return to its original state. The flange fitting recess includes a first portion to be fitted with the flange portion, and a second portion located between the flange portion and the cylindrical body when the first portion is fitted with the flange portion. In the present invention, the second portion is shaped to become gradually smaller in radial dimension as the second portion extends toward the cylindrical body. Herein, the wording "(to be) shaped to become gradually smaller in radial dimension" may mean in other words that the inner wall surface of a wall portion surrounding the second portion of the flange fitting recess constitutes a part of a conical surface having its apex located on the side of the cylindrical body.

When mounting the cartridge, the cylindrical portion is pushed into the cylindrical portion fitting recess through the continuous opening portion while inserting the flange portion of the cartridge into the first portion of the flange fitting recess in order to achieve snap engagement. When removing the cartridge, the cylindrical portion is extracted from the cylindrical portion fitting recess by causing the distal end side of the cylindrical portion to get out from the continuous opening portion while lifting the cylindrical portion using the flange portion as the fulcrum, and thereafter the flange portion is extracted from the flange fitting recess. During this operation, the flange portion can be tilted while sliding on the inner wall surface of a wall portion surrounding the second portion of the flange fitting recess since the second portion is shaped to become gradually smaller in radial dimension as the second portion extends toward the cylindrical body. As a result, the cartridge can be easily removed using the flange portion as the fulcrum. The cartridge fitting portion of such structure can easily be integrally formed with the cylindrical syringe. As a result, according to the present invention, it is possible to provide an applicator made of a resin, which allows for easy mounting and removal of a cartridge with a simple structure and at a low price compared to the conventional ones.

Preferably, a stepped portion to be engaged with the flange portion is formed between the flange fitting recess and the cylindrical portion fitting recess. The stepped portion is preferably configured to entirely contact the end surface of the flange portion located on the side of the cylindrical portion. With adoption of this structure, the flange portion is pressed against the stepped portion when the piston is pressed by the plunger, thereby preventing the cartridge from popping out of the cartridge fitting portion.

Preferably, a sectional shape of an inner wall surface of the wall portion surrounding the cylindrical portion fitting recess has an arcuate profile that is continuous with the continuous opening portion, as the wall portion is cut in a direction orthogonal to a longitudinal direction of the cylindrical syringe, and the arcuate profile has an arcuate angle larger than 180 degrees. With such a structure, a sufficient force for holding the cylindrical portion, which is required for snap engagement, can be secured.

BRIEF DESCRIPTION OF DRAWINGS

FIGS. 1A to 1F are a front view, a bottom view, a plan view, a left side view, a right side view, and a perspective view, respectively, illustrating that an applicator is mounted with a cartridge.

FIG. 4B is a vertical sectional view illustrating the applicator mounted with the cartridge when the plunger is pushed in.

FIG. 6 is an enlarged vertical sectional view illustrating a main portion of the applicator mounted with the cartridge when the plunger is pushed in.

DESCRIPTION OF EMBODIMENTS

Figure 2A:
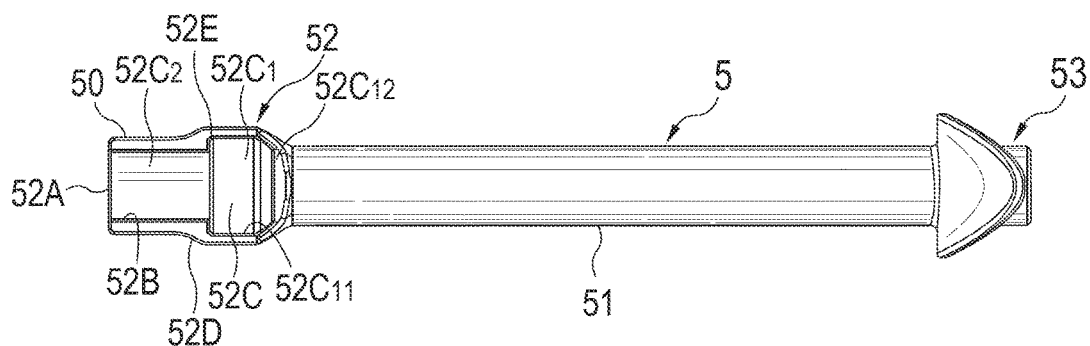
FIGS. 2A to 2D are a bottom view, a right side view, a left side view, and a perspective view, respectively, of a cylindrical syringe.

Now, with reference to the accompanying drawings, an embodiment of the present invention will be described below in detail, wherein the present invention is applied to an applicator used for discharging a paste-type dental material. FIGS. 1A to 1F are a front view, a bottom view, a plan view, a left side view, a right side view, and a perspective view, respectively, illustrating an applicator 1 of the present embodiment mounted with a cartridge 3. The applicator 1 includes a cylindrical syringe 5 and a plunger 7. In FIGS. 1A-1C and 1F, the plunger 7 is located at a stand-by position as discussed later.

<Applicator>

The applicator 1 includes the cylindrical syringe 5 and the plunger 7. As illustrated in FIGS. 1A-1F and 2A-2D, the cylindrical syringe 5 is integrally molded from a resin material such as polypropylene or polyethylene, and has two ends. The cylindrical syringe 5 includes a cartridge fitting portion 52 provided at one 50 of the two ends of the cylindrical syringe 5 and configured to be fitted with the cartridge 3. As illustrated in FIGS. 1A-1F and 3A-3D, the plunger 7 is integrally molded from a resin material such as polypropylene or polyethylene, and has two ends. The plunger 7 includes a pressing portion 72 provided at one 71 of the two ends of the plunger 7 and configured to be inserted into the cylindrical syringe 5 from the other 53 of the two ends of the cylindrical syringe 5 and to press a piston 4 inside the cartridge 3 fitted with the cartridge fitting portion 52, and an operated portion 74 provided at the other 73 of the two ends of the plunger 7, extending through the other end 53 of the cylindrical syringe 5, and configured to be pressed by a finger of an operator. The cylindrical syringe 5 and the plunger 7 are each molded integrally from a resin material, which makes it possible to significantly reduce the price of the applicator 1 compared to the conventional ones.

In the present embodiment, a stopper portion 76 that abuts on the other end 53 of the cylindrical syringe 5 is provided in the vicinity of the operated portion 74 of the plunger 7. Providing such stopper portion 76 in this way prevents the operator from pushing the plunger 7 too far into the cylindrical syringe 5 to break the plunger 7 or the cylindrical syringe 5 which is made of a resin material. The plunger 7 is shaped such that the outer peripheral surface of a portion 77 that is adjacent to the stopper portion 76 is proximate to the inner peripheral surface of the cylindrical syringe 5. With adoption of such structure, the plunger 7 can be stably moved along the cylindrical syringe 5 when the plunger 7 is pushed in. As a result, the plunger 7 is not swung when the plunger 7 is pushed in, thereby improving the operability of the applicator 1. In addition, the plunger 7 advantageously does not easily slip out of the cylindrical syringe 5.

<Resistance Structure>

In the present embodiment, as illustrated in FIGS. 4A-4B, 5A-5B, and 6, a resistance structure (54, 75) is provided between the inner peripheral surface of the cylindrical syringe 5 and the outer peripheral surface of the pressing portion 72 of the plunger 7. The resistance structure (54, 75) acts as resistance to movement of the pressing portion 72 when the pressing portion 72 is moved toward the cartridge fitting portion 52 beyond a predetermined position P shown in FIG. 5A and to movement of the pressing portion 72 when the pressing portion 72 is moved from the side of the cartridge fitting portion 52 toward the other end 53 of the cylindrical syringe 5 beyond the predetermined position P. The resistance structure (54, 75) is configured to allow the pressing portion 72 to be moved beyond the predetermined position P against the resistance when a force equal to or greater than a predetermined force is applied to the plunger 7 in the longitudinal direction of the plunger 7.

Figure 5A:
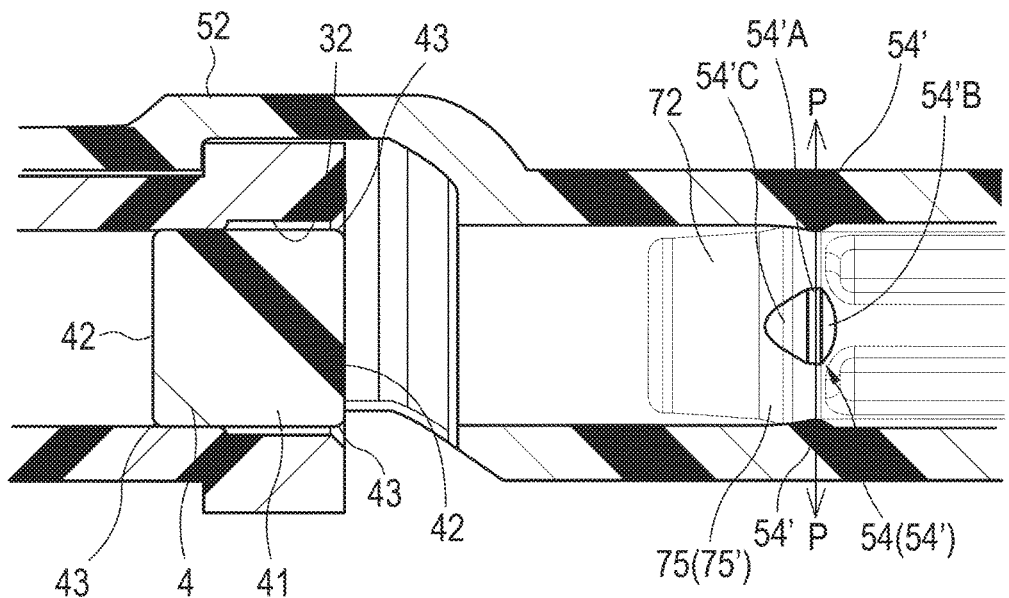
FIG. 5A is an enlarged sectional view illustrating a main portion of the applicator mounted with the cartridge when the plunger is withdrawn; an upper part of FIG. 5B is an enlarged view illustrating the shape of a distributed projecting portion; and a lower part of FIG. 5B is a sectional view as taken along line C-C of the upper part of FIG. 5B.
Figure 6:
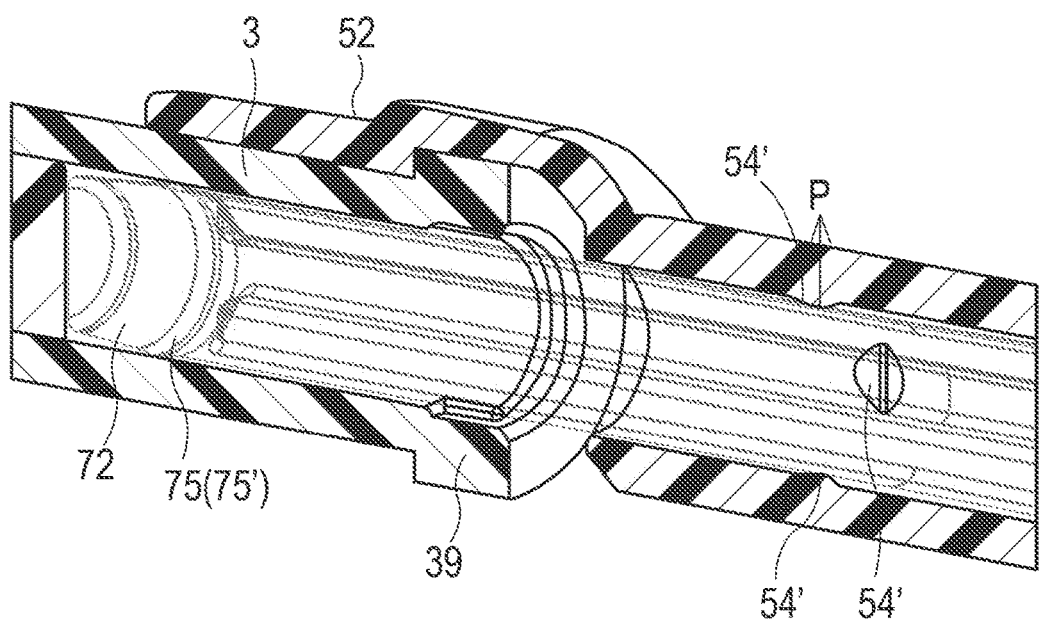

In the embodiment, as illustrated enlargedly in FIGS. 5A and 6, the resistance structure (54, 75) includes at least one outer projecting portion 54 integrally formed with the inner peripheral surface of the cylindrical syringe 5 to project radially inward, and at least one inner projecting portion 75 integrally formed with the outer peripheral surface of the pressing portion 72 of the plunger 7 to project radially outward. The resin material for forming the cylindrical syringe 5 and the shape of the at least one outer projecting portion 54 and the resin material for forming the plunger 7 and the shape of the at least one inner projecting portion 75 are determined such that the at least one inner projecting portion 75 and the at least one outer projecting portion 54 are deformed to allow the at least one inner projecting portion 75 to pass over the at least one outer projecting portion 54 when a force equal to or greater than the predetermined force is applied to the plunger 7. The resin materials are preferably polypropylene. With this configuration, the inner projecting portion 75 and the outer projecting portion 54, which are constituents required for the resistance structure (54, 75), can be integrally formed with the cylindrical syringe 5 and the plunger 7, respectively, when the cylindrical syringe 5 and the plunger 7 are molded.

As illustrated in FIGS. 3A-3D, 5A, and 6, the at least one inner projecting portion 75 provided on the plunger 7 is constituted from one annular projecting portion 75' that continuously annularly extends on the outer peripheral surface of the pressing portion 72 of the plunger 7, and the cross-sectional shape of the annular projecting portion 75' has a mountain-like profile of which the height gradually increases continuously toward the apex of the profile, as the annular projecting portion 75' is cut in a direction orthogonal to the circumferential direction of the plunger 7. The at least one outer projecting portion 54 is constituted from four distributed projecting portions 54' provided at predetermined angular intervals in the circumferential direction. The cross-sectional shape of each distributed projecting portion 54' has a profile of which the height gradually increases continuously toward the apex of the profile, as the distributed projecting portions 54' are cut in a direction orthogonal to the circumferential direction of the cylindrical syringe 5. The cross-sectional shape of each distributed projecting portion 54' has a profile of which the height gradually increases continuously toward the apex of the profile, as the distributed projecting portions 54' are cut in the circumferential direction of the cylindrical syringe 5. The predetermined angular intervals between the plurality of distributed projecting portions 54' may be determined as desired, but are preferably 60°, 90°, or 120°. With these angles, both high molding precision and high strength can be easily achieved even if the cylindrical syringe 5 and the plunger 7 are molded from a resin material.

Figure 5B:
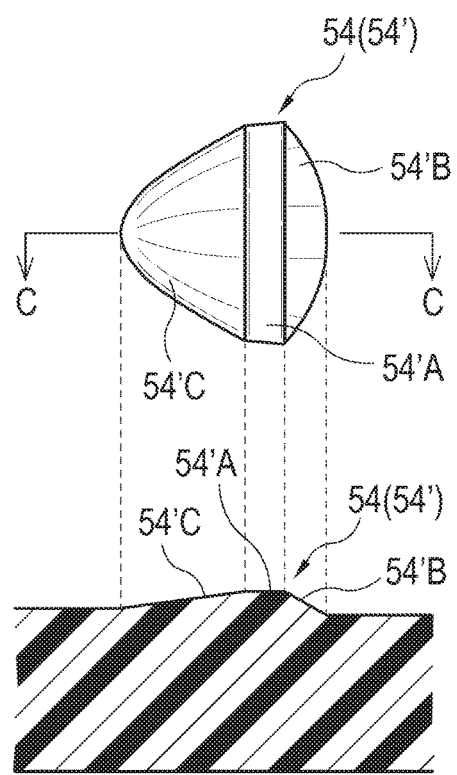

As illustrated enlargedly in FIG. 5B, the profile of each distributed projecting portion 54' has a flat portion 54'A provided at the apex of the profile, and a skirt 54'C formed on the side of the cartridge fitting portion 52 [see FIG. 1A] with respect to the flat portion 54'A is longer than a skirt 54'B formed on the side of the other end 53 [see FIG. 1A] of the cylindrical syringe 5 with respect to the flat portion 54'A. If the distributed projecting portions 54' include the flat portion 54'A, the apexes of the distributed projecting portions 54' are more uniformly worn when either one of the annular projecting portion 75' and the four distributed projecting portions 54' passes over the other. This prevents the apexes of the distributed projecting portions 54' from being worn out early even if an action of either one of the annular projecting portion and the plurality of distributed projecting portions passing over the other or a converse action is repeatedly performed a certain number of times. As a result, the applicator 1 can be used a plurality of times even if the cylindrical syringe 5 and the plunger 7 are molded from a resin material. Providing the flat portion 54'A on each distributed projecting portion 54' can increase the processing precision of the distributed projecting portion 54'.

In contrast, the resistance structure according to the embodiment described above, the at least one outer projecting portion 54 may be constituted from one annular projecting portion that continuously annularly extends on the inner peripheral surface of the cylindrical syringe 5, and the cross-sectional shape of the annular projecting portion may have a mountain-like profile of which the height gradually increases continuously toward the apex of the profile, as the annular projecting portion is cut in a direction orthogonal to the circumferential direction of the cylindrical syringe 5. In this configuration, the at least one inner projecting portion 75 may be constituted from a plurality of distributed projecting portions provided at predetermined angular intervals in the circumferential direction of the plunger 7, and the cross-sectional shape of each distributed projecting portion may have a profile of which the height gradually increases continuously toward the apex of the profile, as the distributed projecting portions are cut in the direction orthogonal to the circumferential direction of the plunger 7 and the cross-sectional shape of each distributed projecting portion may have a profile of which the height gradually increases continuously toward the apex of the profile, as the distributed projecting portions are cut in the circumferential direction of the plunger 7.

In a configuration as in the present embodiment, wherein the resistance structure (54, 75) is constituted from the one annular projecting portion 75' and the plurality of distributed projecting portions 54', the annular projecting portion 75' and the plurality of distributed projecting portions 54' can be easily deformed when a force equal to or greater than a predetermined force is applied to the plunger 7 in the longitudinal direction of the plunger 7 as either one of the annular projecting portion 75' and the plurality of distributed projecting portions 54' passes over the other. In contrast, after either one of the annular projecting portion 75' and the plurality of distributed projecting portions 54' has passed over the other, either one of the annular projecting portion 75' and the plurality of distributed projecting portions 54' does not pass over the other in the opposite direction, even if the plunger 7 is rotated in the cylindrical syringe 5, unless a predetermined force is applied to the plunger 7 in the longitudinal direction of the plunger 7. Thus, the plunger 7 can be prevented from slipping off with a simple structure.

The position P of the resistance structure (54, 75) may be determined as desired. Preferably however, the resistance structure is provided adjacent to the cartridge fitting portion 52 of the cylindrical syringe 5 as in the present embodiment. If the resistance structure is located at the position P, it is possible to reduce the distance by which the plunger 7 is moved downward from the cylindrical syringe 5 when the operator holds the applicator 1 with the plunger 7 being directed downward, thereby improving the operability of the applicator 1. In practice, the resistance structure (54, 75) is preferably positioned such that the cartridge 3 can be fitted with the cartridge fitting portion 52 and the cartridge 3 can be removed from the cartridge fitting portion 52 when the at least one inner projecting portion 75 of the plunger 7 is in contact with the at least one outer projecting portion 54. With this configuration, the cartridge 3 can be mounted and removed without removing the plunger 7.

<Cartridge>

Figure 7A:
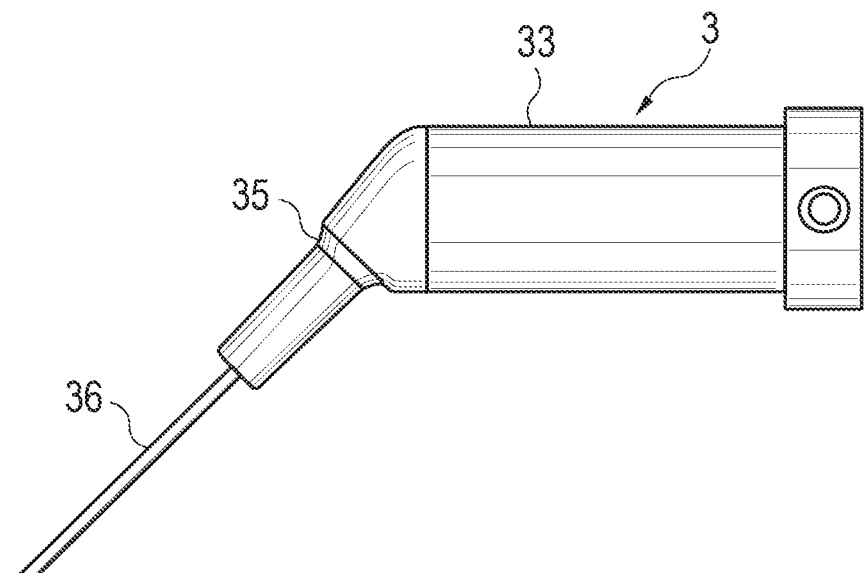
FIG. 7A is a front view of the cartridge.
Figure 7B:
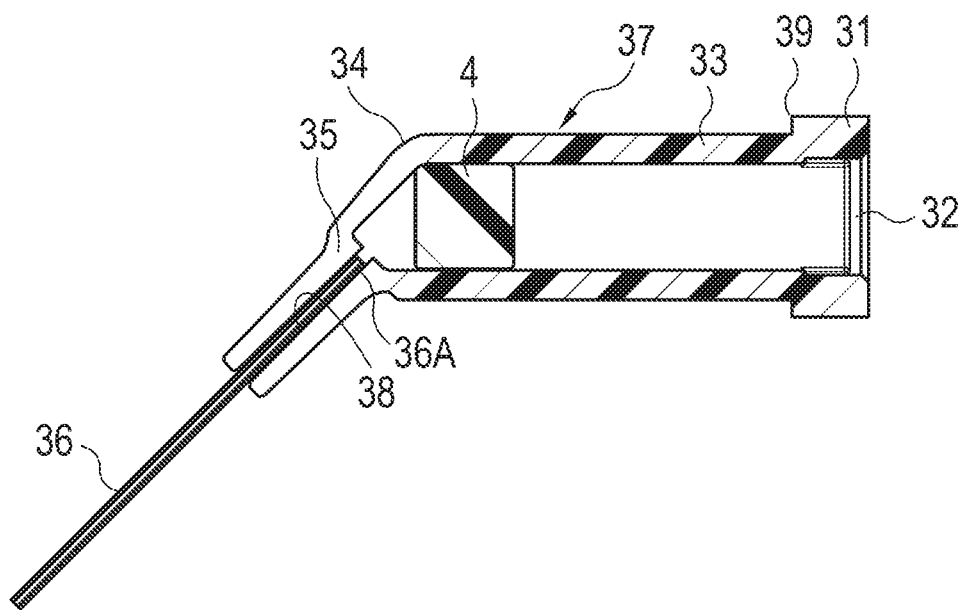
FIG. 7B is a vertical sectional view of the cartridge.
Figure 8:
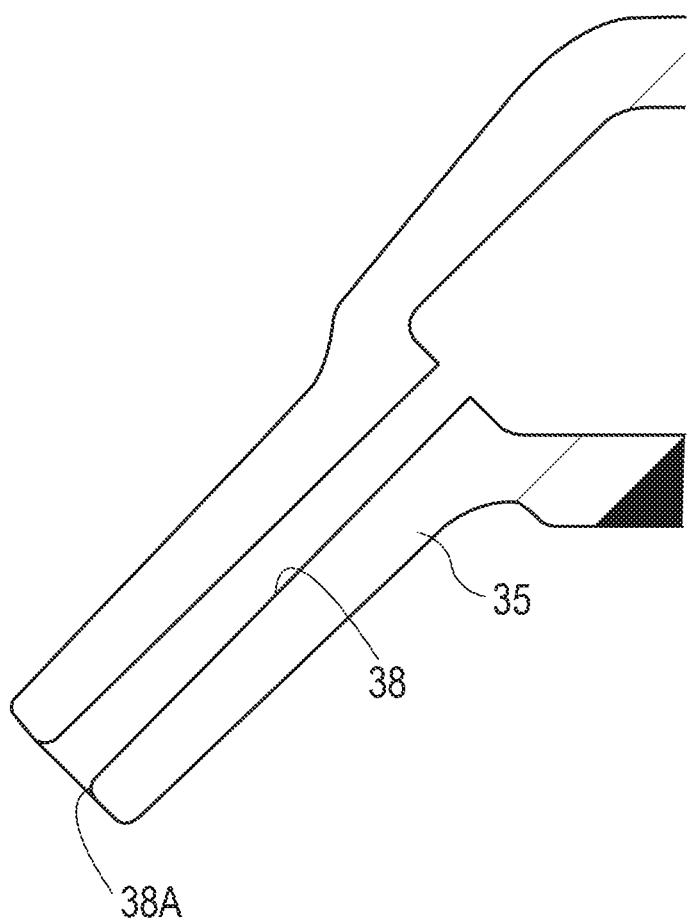
FIG. 8 is an enlarged vertical sectional view of a nozzle portion of the cartridge.

As illustrated in FIGS. 7A and 7B, the cartridge 3 includes a cylindrical portion 33 having two ends and an opening portion 32 and a flange portion 39 formed at one 31 of the two ends of the cylindrical portion 33, a nozzle portion 35 provided at the other 34 of the two ends of the cylindrical portion 33, and the piston 4 disposed inside the cylindrical portion 33 to push out a content contained in the cylindrical portion 33 from the nozzle portion 35. The nozzle portion 35 includes, as a nozzle, a pipe 36 made of metal and provided at the other end 34 of the cylindrical portion 33. The cylindrical portion 33 and the nozzle portion 35 are integrally molded from a resin material such as polypropylene. Preferably, an entire surface of the end portion 36A of the pipe 36 is curved such that no angled portion is present. With this configuration, it is possible to prevent the inner wall of a through hole 38 from being shaved by the pipe 36 when inserting the pipe 36 into the through hole 38, thereby furthermore preventing the swarf from being produced and pushed out as mixed in the content. As illustrated in FIG. 8, an annular tapered surface 38A is formed at an entrance portion of the through hole 38, and the tapered surface 38A becomes larger in radial dimension toward an opening end surface of the entrance portion. The tapered surface 38A is formed not to contact the outer peripheral surface of the pipe 36 when the pipe 36 is press-fitted into the through hole 38. Such a tapered surface 38A facilitates insertion of the pipe 36 into the through hole 38.

The through hole 38 is shaped such that the radial dimension of the through hole 38, which extends in the longitudinal direction of the nozzle portion 35 continuously with the tapered surface 38A, becomes gradually smaller and thereafter constant. With this configuration, the pipe 36 can be easily inserted to the middle of the through hole 38, after which the pipe 36 is press-fitted, thereby alleviating the workload of press-fitting.

Figure 9A:
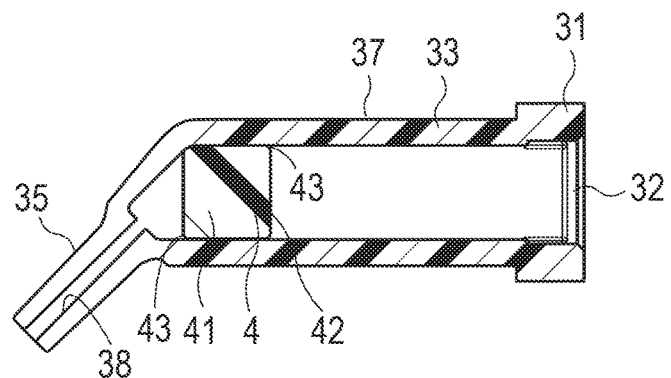
FIGS. 9A and 9B are a vertical sectional view and a horizontal sectional view, respectively of the cartridge.
Figure 9B:
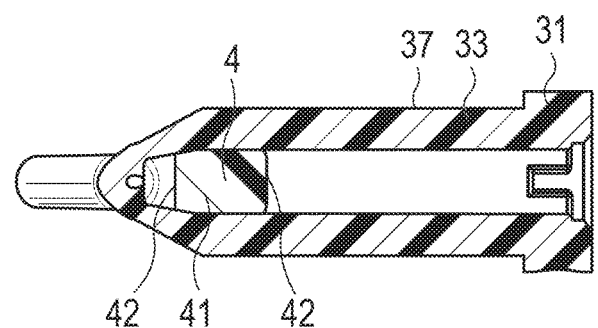
Figure 9C:
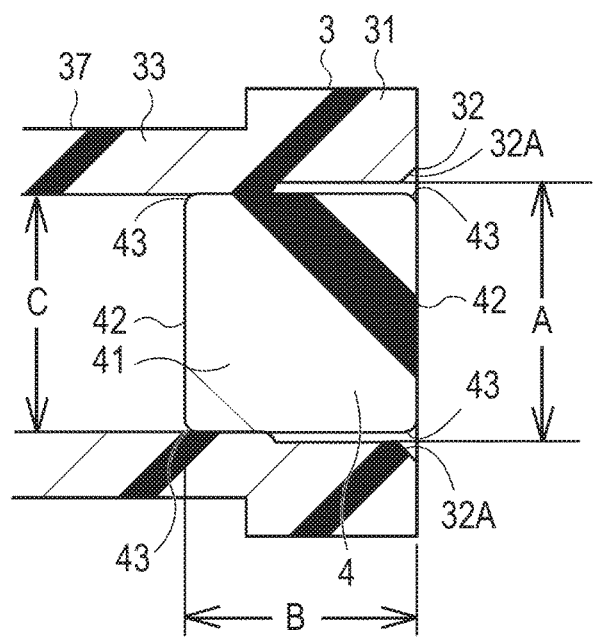
FIG. 9C is a sectional view illustrating a main portion of the applicator including a piston.

The piston 4 is integrally molded from a resin material such as polypropylene. As illustrated in FIGS. 9A to 9C, a pair of piston-side tapered surfaces 43 or piston-side curved surfaces 43 are formed between an annular peripheral wall surface 41 of the piston 4 and a pair of circular end surfaces 42, 42 of the piston 4 located on both sides in the thickness direction of the piston 4. The pair of piston-side tapered surfaces 43 or piston-side curved surfaces 43 become smaller in radial dimension from the annular peripheral wall surface 41 toward the pair of circular end surfaces 42, 42. In FIGS. 9A and 9B, one of the end portions of the piston 4 has been deformed to conform to the shape of the inner wall surface of the cylindrical portion 33 of a cartridge body 37.

As illustrated in FIG. 9C, a body-side tapered surface 32A or a body-side curved surface 32A is formed at the opening portion 32 at the one end of the cylindrical portion 33 of the cartridge body 37, and the body-side tapered surface 32A or the body-side curved surface 32A becomes smaller in radial dimension toward the other end of the cylindrical portion 33. The inner angle of the body-side tapered surface 32A or the radius of curvature of the body-side curved surface 32A is larger than the inner angle of the pair of piston-side tapered surfaces 43 or the radius of curvature of the pair of piston-side curved surfaces 43 formed on the piston 4. This configuration further facilitates insertion of the piston 4 from the opening portion 32 of the cylindrical portion 33.

<Structure of Cartridge Fitting Portion>

Figure 2B:
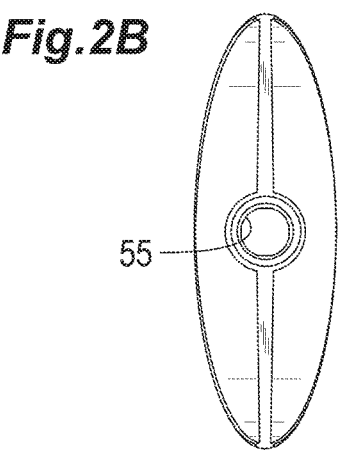
Figure 2C:
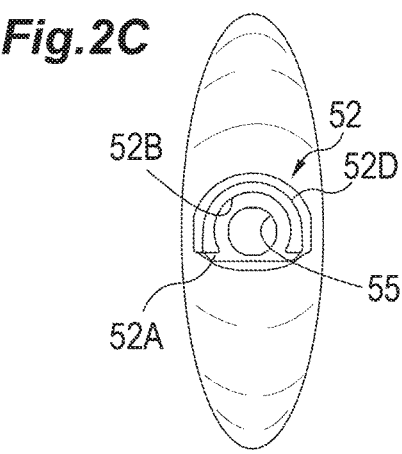
Figure 2D:
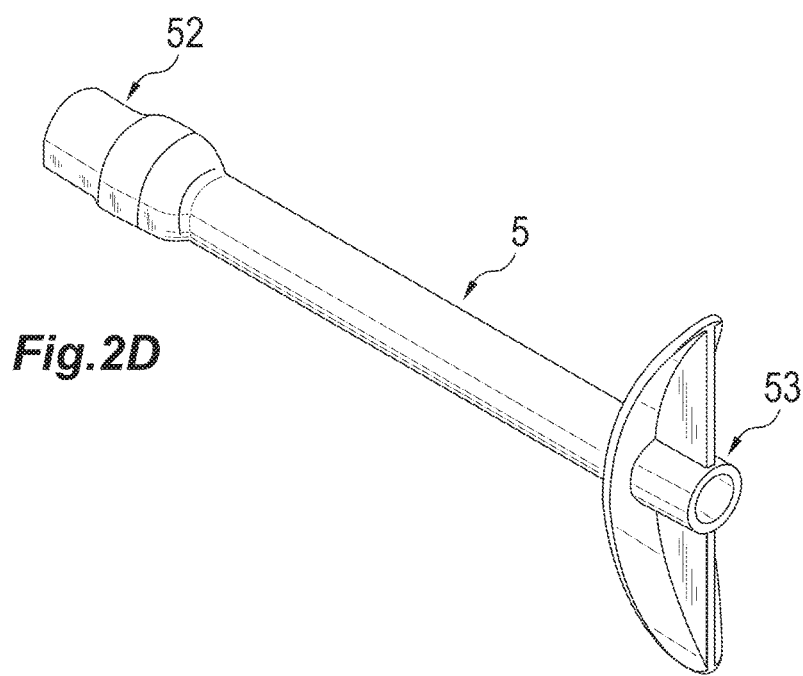
Figure 3A:
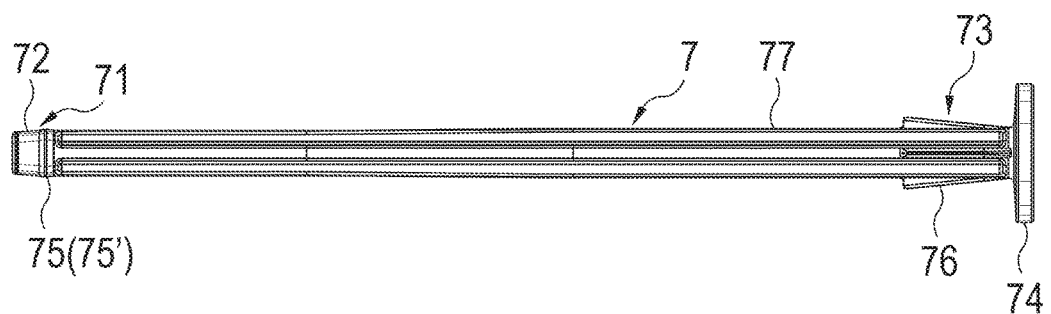
FIGS. 3A to 3D are a front view, a left side view, a right side view, and a perspective view, respectively, of a plunger.
Figure 3B:
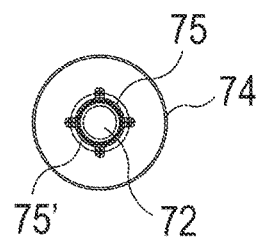
Figure 3C:
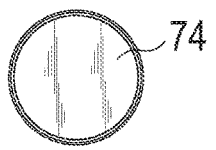
Figure 3D:
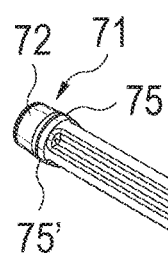
Figure 3D:
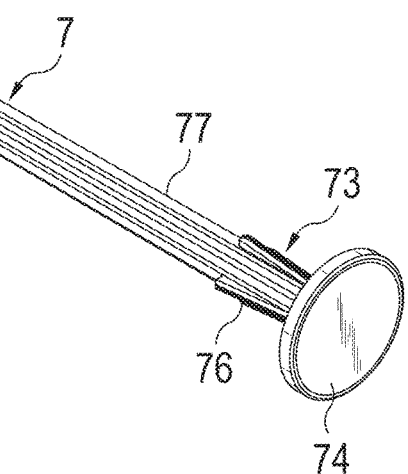
Figure 4A:
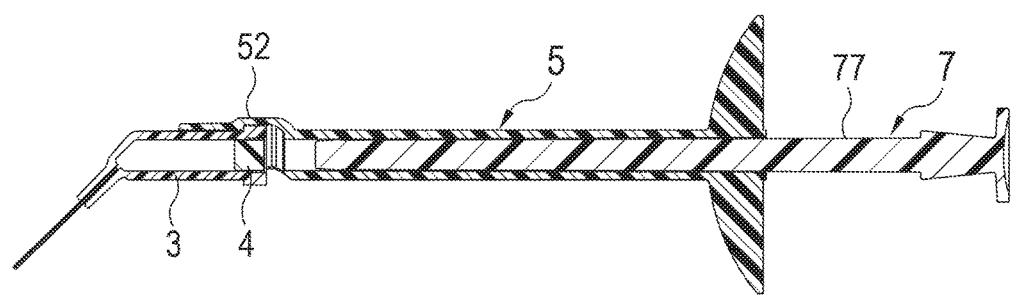
FIG. 4A is a vertical sectional view illustrating the applicator mounted with the cartridge when the plunger is withdrawn.
Figure 4B:
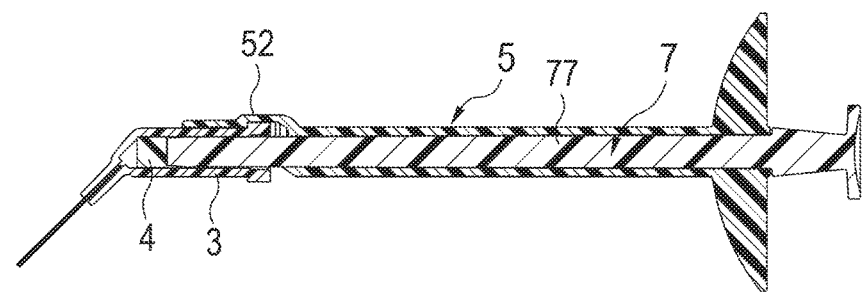

As illustrated in FIGS. 2A and 2B, the cartridge fitting portion 52 configured to be fitted with the cartridge 3 includes an end surface opening portion 52A opened in an extending direction in which a cylindrical body 51 of the cylindrical syringe 5 extends, a continuous opening portion 52B continuous with the end surface opening portion 52A, opened in a radial direction, and extending in the extending direction, and a recess portion 52C configured to communicate with the continuous opening portion 52B and an internal passage 55 in the cylindrical body 51. The recess portion 52C includes a flange fitting recess 52C1 to be fitted with the flange portion 39 of the cartridge 3, and a cylindrical portion fitting recess 52C2 configured to communicate with the flange fitting recess 52C1 and to be fitted with a part of the cylindrical portion 33. A wall portion 52D surrounding the cylindrical portion fitting recess 52C2 of the cartridge fitting portion 52 is configured to warp into snap engagement with the part of the cylindrical portion 33 when the part of the cylindrical portion 33 is inserted from the continuous opening portion 52B. Specifically, a sectional shape of an inner wall surface of the wall portion 52D surrounding the cylindrical portion fitting recess 52C2 has an arcuate profile that is continuous with the continuous opening portion 52B, as the wall portion 52D is cut in a direction orthogonal to a longitudinal direction of the cylindrical syringe 5, and the arcuate profile has an arcuate angle larger than 180 degrees. With such a structure, a sufficient force for holding the cylindrical portion 33, which is required for snap engagement, can be secured. The term "snap engagement" refers to engagement obtained when the wall portion 52D surrounding the cylindrical portion fitting recess 52C2 holds the cylindrical portion 33 utilizing a force generated in the wall portion 52D which has been deformed to be opened and then is going to return to its original state. The flange fitting recess 52C1 includes a first portion 52C11 to be fitted with the flange portion 39, and a second portion 52C12 located between the flange portion 39 and the cylindrical body 51 when the first portion 52C11 is fitted with the flange portion 39. In the present embodiment, the second portion 52C12 is shaped to become gradually smaller in radial dimension as the second portion 52C12 extends toward the cylindrical body 51. The wording "(to be) shaped to become gradually smaller in radial dimension" may mean in other words that the inner wall surface of a wall portion surrounding the second portion 52C12 of the flange fitting recess 52C1 constitutes a part of a conical surface having its apex located on the side of the cylindrical body 51.

A stepped portion 52E to be engaged with the flange portion 39 is formed between the flange fitting recess 52C1 and the cylindrical portion fitting recess 52C2. The stepped portion 52E is configured to entirely contact the end surface of the flange portion 39 located on the side of the cylindrical portion 33. With adoption of this structure, the flange portion 39 is pressed against the stepped portion 52E when the piston 4 is pushed by the plunger 7, thereby preventing the cartridge 3 from popping out of the cartridge fitting portion 52.

Figure 10A:
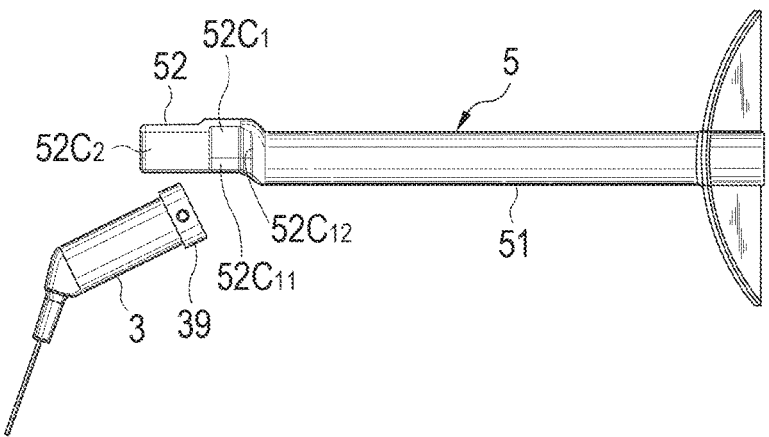
FIGS. 10A to 10C illustrate how the cartridge is mounted to the applicator.
Figure 10B:
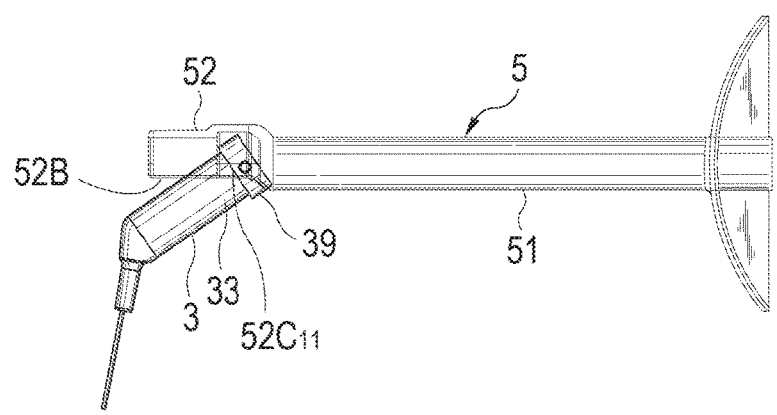
Figure 10C:
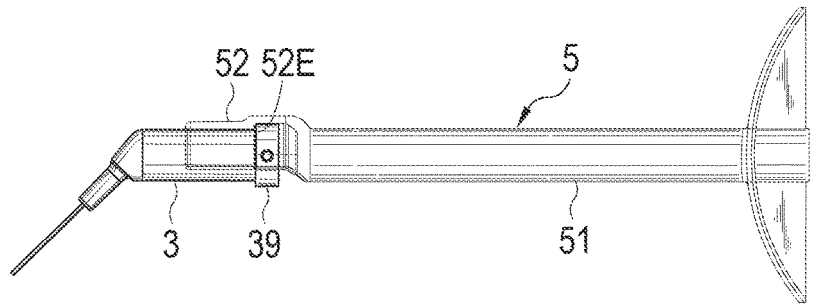

When mounting the cartridge 3, as illustrated in FIGS. 10A and 10B, the cylindrical portion 33 is pushed into the cylindrical portion fitting recess 52C2 through the continuous opening portion 52B while inserting the flange portion 39 of the cartridge 3 into the first portion 52C11 of the flange fitting recess 52C1 in order to achieve snap engagement. When removing the cartridge 3, the cylindrical portion 33 is extracted from the cylindrical portion fitting recess 52C2 by causing the distal end side of the cylindrical portion 33 to get out from the continuous opening portion 52B while lifting up the cylindrical portion 33 using the flange portion 39 as the fulcrum, and thereafter the flange portion 39 is extracted from the flange fitting recess 52C1. During this operation, the flange portion 39 can be tilted while sliding on the inner wall surface of a wall portion surrounding the second portion 52C12 of the flange fitting recess 52C1 since the second portion 52C12 is shaped to become gradually smaller in radial dimension as the second portion 52C12 extends toward the cylindrical body 51. As a result, the cartridge 3 can be easily removed using the flange portion 39 as the fulcrum. The cartridge fitting portion 52 of such structure can easily be integrally formed with the cylindrical syringe 5. As a result, it is possible to provide an applicator made of a resin material with ease and at a low price.

While the preferred embodiments of the present invention have been described and shown herein, the present invention should not be construed in a limiting sense. It should be understood that various modifications, rearrangements, and substitutions may be made without departing from the scope of the present invention.

INDUSTRIAL APPLICABILITY

The structure of the cartridge fitting portion of the applicator according to the present invention enables ready mounting and removal of a cartridge, thereby providing an applicator made of a resin and with a simple structure at a lower cost than the conventional applicators.

What is claimed is:

1. An applicator comprising:
a cylindrical syringe made of a resin and including a cylindrical body having two ends, the cylindrical body including a cartridge fitting portion at one of the two ends of the cylindrical body, the cartridge fitting portion being configured to be fitted with a cartridge which includes a cylindrical portion having two ends, having an opening portion and a flange portion at one of the two ends of the cylindrical portion, a nozzle portion provided at the other of the two ends of the cylindrical portion, and a piston disposed inside the cylindrical portion to push out a content contained in the cylindrical portion from the nozzle portion; and
a plunger made of a resin, having two ends, and including a pressing portion provided at one of the two ends of the plunger and configured to be inserted into the cylindrical syringe from the other of the two ends of the cylindrical body of the cylindrical syringe and to press the piston inside the cartridge fitted with the cartridge fitting portion, and an operated portion provided at the other of the two ends of the plunger, extending through the other end of the cylindrical body of the cylindrical syringe, and configured to be pressed by a finger of an operator, wherein:
the cartridge fitting portion includes an end surface opening portion opened in an extending direction in which the cylindrical body extends, a continuous opening portion continuous with the end surface opening portion, opened in a radial direction, and extending in the extending direction, and a recess portion configured to communicate with the end surface opening portion, the continuous opening portion, and an internal passage in the cylindrical body;
the recess portion includes a flange fitting recess to be fitted with the flange portion of the cartridge, and a cylindrical portion fitting recess configured to communicate with the flange fitting recess and to be fitted with a part of the cylindrical portion;
a wall portion surrounding the cylindrical portion fitting recess of the cartridge fitting portion is configured to warp into snap engagement with the part of the cylindrical portion when the part of the cylindrical portion is inserted from the continuous opening portion;
the flange fitting recess includes a first portion to be fitted with the flange portion, and a second portion located between the flange portion and the cylindrical body when the first portion is fitted with the flange portion;
a sectional shape of an inner wall surface of the wall portion surrounding the cylindrical portion fitting recess has an arcuate profile that is continuous with the continuous opening portion, as the wall portion is cut in a direction orthogonal to a longitudinal direction of the cylindrical syringe;
the arcuate profile has an arcuate angle larger than 180 degrees; and,
an inner wall surface of a wall portion surrounding the second portion of the flange fitting recess is shaped to become gradually smaller in radial dimension as the second portion extends toward the cylindrical body such that the flange portion is tilted to slide on the inner wall surface when extracting the cylindrical portion from the cylindrical portion fitting recess by causing the distal end side of the cylindrical portion to get out from the continuous opening portion while lifting the cylindrical portion using the flange portion as the fulcrum.

2. The applicator according to claim 1, wherein:
a stepped portion to be engaged with the flange portion is formed between the flange fitting recess and the cylindrical portion fitting recess; and
the stepped portion is configured to entirely contact the end surface of the flange portion located on the side of the cylindrical portion.

* * * * *